United States Patent [19]

Schmidt et al.

[11] Patent Number: 4,533,674

[45] Date of Patent: Aug. 6, 1985

[54] PROCESS FOR PREPARING A SUGAR AND STARCH FREE SPRAY-DRIED VITAMIN C POWDER CONTAINING 90 PERCENT ASCORBIC ACID

[75] Inventors: Douglass N. Schmidt, Grosse Ile; Jeffrey L. Finnan, Southgate; Rudolph E. Lisa, Grosse Ile, all of Mich.

[73] Assignee: BASF Wyandotte Corporation, Wyandotte, Mich.

[21] Appl. No.: 544,608

[22] Filed: Oct. 24, 1983

[51] Int. Cl.$^3$ .......................................... A61K 31/365
[52] U.S. Cl. ................................................... 514/474
[58] Field of Search ........................................ 424/280

[56] References Cited

U.S. PATENT DOCUMENTS

| | | | |
|---|---|---|---|
| 3,266,992 | 8/1966 | de Jong | 424/280 |
| 3,293,132 | 12/1966 | Stoyle et al. | 424/280 |
| 3,396,226 | 8/1968 | Cavalli et al. | 424/280 |
| 3,852,421 | 12/1974 | Koyanagi et al. | 424/280 |
| 4,036,948 | 7/1977 | Kitamori et al. | 424/280 |
| 4,352,821 | 10/1982 | Doran et al. | 424/361 |
| 4,372,968 | 2/1983 | Kitamori et al. | 424/280 |
| 4,389,393 | 6/1983 | Schor et al. | 424/19 |
| 4,454,125 | 6/1984 | Demopoulos | 424/280 |
| 4,486,435 | 12/1984 | Schmidt et al. | 424/280 |

OTHER PUBLICATIONS

Chem. Abst. 99, 218464(v) (1983), Velikova et al.

*Primary Examiner*—Douglas W. Robinson
*Attorney, Agent, or Firm*—David L. Hedden; Joseph D. Michaels

[57] ABSTRACT

The subject invention relates to a vitamin C powder prepared by (a) spray drying an aqueous slurry of ascorbic acid and binder in the presence of an absorbent in amounts such that the resulting powder will contain at least 90 percent by weight of ascorbic acid, no more than 9 percent by weight of binder, from 0.2 to 2 percent by weight of absorbent; and blending from 0.2 to 5 percent by weight of a lubricant into the powder prepared by step (a). Preferably microcrystalline cellulose and mixtures of microcrystalline cellulose and hydroxypropylmethylcellulose are used as the binder.

The resulting sugar and starch free vitamin C powder prepared by this process will be free flowing, have an ascorbic acid content of at least 90 percent by weight, be color stable under use conditions, will contain a lubricant, and is directly compressible into tablets which have acceptable hardness, friability, color stability, and disintegration times.

3 Claims, No Drawings

PROCESS FOR PREPARING A SUGAR AND STARCH FREE SPRAY-DRIED VITAMIN C POWDER CONTAINING 90 PERCENT ASCORBIC ACID

BACKGROUND OF THE INVENTION

1. Field of the Invention

This invention relates to vitamin C powders prepared by spray drying an aqueous slurry of ascorbic acid and a binder in the presence of an absorbent.

2. Description of the Prior Art

U.S. Pat. No. 3,396,226 relates to compositions which are suitable for direct compression into tablets without prior granulation procedures. The compositions consist of a mixture of (1) from about 60 percent to about 80 percent by weight of ascorbic acid, (2) from about 19 percent to 50 percent by weight of microcrystalline cellulose, and (3) at least one lubricant selected from the group consisting of metallic stearates and other similar compounds. The ascorbic acid has a particle size such that not more than 60 percent by weight thereof is retained on a 100 mesh screen, from about 10 percent to about 50 percent by weight thereof is retained on a 200 mesh screen, and from about 30 to 75 percent by weight thereof is passable through a 200 mesh screen. The compositions described in this patent are prepared by mixing or blending.

One of the problems with this method is that the resulting tablets have high amounts of microcrystalline cellulose and, consequently, low amounts (no more than 80 percent by weight) of ascorbic acid. Furthermore, the process used in making the composition is not a continuous one.

U.S. Pat. No. 3,293,132 describes a continuous process for making a vitamin C powder by spray drying. The process involves spray drying from 75 to 95 parts by weight of ascorbic acid, from 5 to 25 parts by weight of a carbohydrate, and from 0.5 to 5 parts by weight of a filmproducing hydrophilic, organic colloid material such as gelatin, water-soluble derivatives of casein, water-soluble gums, and water-soluble derivatives of cellulose. Although the process is continuous, it has the disadvantage of utilizing a carbohydrate such as a sugar, for example, lactose, sucrose, maltose, glucose, etc., which are not desirable in the vitamin C powder and tablet for nutritional reasons.

SUMMARY OF THE INVENTION

The subject invention relates to a vitamin C powder prepared by (a) spray drying an aqueous slurry of ascorbic acid and binder in the presence of an absorbent in amounts such that the resulting powder will contain at least 90 percent by weight of ascorbic acid, no more than 9 percent by weight of binder, from 0.2 to 2 percent by weight of absorbent; and (b) blending from 0.2 to 5.0 percent by weight of a lubricant into the powder prepared by step (a). Preferably microcrystalline cellulose or a mixture of microcrystalline cellulose and hydroxypropylmethylcellulose are used as the binder.

The resulting vitamin C power prepared by this process will be free flowing, sugar and starch free, have an ascorbic acid content of at least 90 percent by weight, be color stable under use conditions, will contain a lubricant, and is directly compressible into tablets which have acceptable hardness, friability, color stability, and disintegration times.

DESCRIPTION OF THE PREFERRED EMBODIMENT

The vitamin C powdders of this invention are prepared by spray drying an aqueous slurry of absorbic acid and binder in the presence of an absorbent. A lubricant is then added to the resulting powder. The particle size of the ascorbic acid which can be used may vary over wide ranges. However, it is preferred that not more than about 60 percent by weight is retained on a 100 mesh screen, and at least about 30 percent by weight passes through a 200 mesh screen.

Typical binders that can be used include proteins such as gelatin, water-soluble derivatives of casein, e.g., sodium caseinate, and the like; water-soluble gums such as gum acacia, gum karaya, gum ghatti, tragacanth, and the like; cellulose, and water-soluble derivatives of cellulose such as methylcellulose, hydroxyethyl cellulose, sodium carboxymethylcellulose, and the like. For this purpose, use may furthermore be made of certain polyvinyl resins such as, for example, polyvinyl alcohol, polyvinyl pyrrolidine and the like. Preferably used, however, are microcrystalline cellulose, and more preferably, mixtures of microcrystalline cellulose and hydroxypropylmethylcellulose.

To prepare the aqueous slurry, the ascorbic acid and binder are added to enough water to make a finished feed slurry having about 20 to 90 percent solids by weight, and, preferably, about 50 to 75 percent by weight solids.

The aqueous slurry containing the ascorbic acid and binder is spray dried in the presence of an absorbent, preferably silicon dioxide. Preferably used as the absorbent is silicon dioxide of a colloidal particle size, i.e., from 1 nanometer (millimicron) to 1 micron. More preferably used is a silicon dioxide, containing less than 0.2 percent by weight of other materials, of an average primary particle size of 12 nanometers, a surface area of about 200 square meters per gram, a tap density of about 50 grams per liter, a moisture content of 1.5 percent by weight (2 hours at 105° C.), one ignition loss of 1 percent by weight (2 hours at 1000° C.) and a pH of 3.6 to 4.3 (4 percent by weight aqueous dispersion).

As was indicated previously, a lubricant is blended with the spray dried powder after the spray drying is complete. Preferably used as the lubricant are stearic acid, magnesium stearate and mixtures thereof. However, other stearic acids salts may be used such as calcium stearate. Also, there can be used wax-like materials, for instance, wax-like saturated fatty acids, wax-like mixtures containing two or more saturated fatty acids or wax-like hydrogenated glyceride, in admixture with a metallic stearate and/or titanium dioxide.

The components described herein are added in amounts such that the final powder formed will contain at least 90 percent by weight of ascorbic acid, less than 9 percent by weight of binder, 0.2 to 2 percent by weight of silicon dioxide, 0.2 to 5 percent by weight of the lubricant and less than 3 percent of other excipients such as hydroxypropylmethylcellulose.

Any suitable spray drier may be used to prepare the powders of this invention. Preferably used is a vertical spray drier equipped with a means of making droplets, such as a rotary atomizer operated between 10,000 and 35,000 rpm, preferably 18,000 to 25,000 rpm. The inlet temperature is maintained at 190° to 200° C. and the outlet temperature is a function of the inlet temperature and flow rate, generally between 90° C. to 100° C. From 0.5 to 2.5 percent by weight, based on the weight of the dry powder of silicon dioxide is added to the spray drier chamber, preferably at a point of negative pressure. The aqueous slurry of ascorbic acid and binder is then spray dried to form a free-flowing, nonagglomerated powder.

Tablets from the powder are made by conventional methods. Useful tabletting aids are disclosed in *Pharmaceutical Technology,* July, 1980, pages 27-35, and 62.

The examples which follow will provide more details regarding how to practice the invention. In the examples, unless otherwise stated, all parts are by weight and all temperature are in degrees centigrade.

EXAMPLE 1

An aqueous slurry containing 60 percent by weight solids was formed by adding 9286 parts of ascorbic acid and 714 parts of microcrystalline cellulose to water held in a stainless steel jacketed tank equipped with an turbine agitator. The aqueous slurry was sprayed into a four foot diameter vertical spray drier through a rotary atomizer at 20,000 to 23,000 revolutions per minute. About 1.0 percent by weight of silicon dioxide (sold under the trade name AEROSIL 200) was added into the drying chamber at a point of negative pressure. To the spray dried powder, 1.0 percent by weight of magnesium stearate was blended.

The resulting powder contained:

| Component | Percent by Weight Based on the Weight of the Dry Powder |
| --- | --- |
| Ascorbic acid | 90.0 |
| Microcrystalline cellulose | 7.0 |
| Silicon dioxide | 1.0 |
| Magnesium stearate | 1.0 |
| Moisture | 1.0 |

The particle size of the powder was such that 20 to 60 percent of the powder was retained on a 200 mesh screen, 20 to 40 percent of the powder was retained on a 325 mesh screen, and 5 to 30 percent of the powder was able to pass through a 325 mesh screen.

Tablets were made on an eight-station rotary tablet press at 30 revolutions per minute. The resulting tablets had a hardness of 15.7 (SCU), a friability percent of 2.53 which was measured as loss after 120 revolutions in a Vandercamp friabilator, and a disintegration time of 4.5 minutes in water at 37° C. in a Vandercamp disintegration/dissolution tester.

EXAMPLE 2

A suspension was made in a stainless steel jacketed tank equipped with an anchor agitator by adding 48 parts of hydroxymethylcellulose to water such that the resulting suspension had a solids weight of 8.8 percent by weight. The suspension was heated to about 80° C. and then cold water was added in amount such that the suspension had 2.9 percent solids. Then 2200 parts of ascorbic acid and 274 parts of microcrystalline cellulose were added.

The resulting slurry was sprayed into a 30 foot diameter vertical spray drier through a rotary atomizer at 10,000 to 14,000 revolutions per minute in the presence of about 1.0 percent by weight of silicon dioxide (sold under the trade name AEROSIL 200).

The resulting yield was 2410 parts of a spray dried powder which contained:

| Component | Percent by Weight Based on the Weight of the Dry Powder |
| --- | --- |
| Ascorbic Acid | 90.1 |
| Microcrystalline cellulose | 6.4 |
| Hydroxypropylmethylcellulose | 2.0 |
| Silicon dioxide | 1.0 |
| Moisture | 0.5 |

Before tabletting, the powder was mixed with an amount of stearic acid equal to 2.0 percent of the total powder weight.

The resulting tablets had a hardness of 15.0 (SCU), a friability of 2.0 percent, and a disintegration time of 21 minutes.

COMPARISON EXAMPLE

Example 1 was followed except the components were dry-blended instead of spray dried. The resulting powder could not be tabletted.

This comparative example illustrates the need for spray drying in order to produce a powder which has at least a 90 percent ascorbic acid content and is directly compressible into tablets having an acceptable hardness, friability, and disintegration time.

The embodiments of the invention in which an exclusive property or privilege is claimed are defined as follows:

1. A process for preparing a free flowing, sugar free vitamin C powder which is color stable at use conditions, is compressible into tablets, comprising spray drying, in the absence of a lubricant, an aqueous slurry of ascorbic acid and binder in the presence of a silicon dioxide absorbent in amounts such that the resulting powder comprises at least 90 percent by weight of ascorbic acid, from 0 to 9 percent by weight of binder, from 0.5 to 2.0 percent by weight of absorbent.

2. The process of claim 1 wherein the binder is microcrystalline cellulose.

3. The process of claim 2 wherein from 1.0 to 3.0 percent by weight of hydroxypropylmethylcellulose is used as an additional binder.

* * * * *